United States Patent
Darois et al.

(10) Patent No.: US 10,548,703 B2
(45) Date of Patent: Feb. 4, 2020

(54) SOFT TISSUE REPAIR PROSTHESIS, EXPANDABLE DEVICE, AND METHOD OF SOFT TISSUE REPAIR

(71) Applicant: C.R. Bard, Inc., Murray Hill, NJ (US)

(72) Inventors: Roger E. Darois, Foster, RI (US); John Peter Groetelaars, Barrington, RI (US); Michael F. Jacene, Blackstone, MA (US); Anthony Colesanti, Bristol, RI (US); Michael J. Lee, Barrington, RI (US); Richard V. Longo, North Kingstown, RI (US); Tara Smith, Wakefield, RI (US); James M. Brann, East Greenwich, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 303 days.

(21) Appl. No.: 15/299,578

(22) Filed: Oct. 21, 2016

(65) Prior Publication Data

US 2017/0100229 A1    Apr. 13, 2017

Related U.S. Application Data

(63) Continuation of application No. 13/130,625, filed as application No. PCT/US2009/006223 on Nov. 20, 2009, now Pat. No. 9,504,548.

(60) Provisional application No. 61/247,163, filed on Sep. 30, 2009, provisional application No. 61/199,884, filed on Nov. 21, 2008.

(51) Int. Cl.
*A61F 2/00*    (2006.01)

(52) U.S. Cl.
CPC .... *A61F 2/0063* (2013.01); *A61F 2002/0072* (2013.01)

(58) Field of Classification Search
CPC .......... A61F 2/0063; A61F 2002/0072; A61B 2017/00623
See application file for complete search history.

(56) References Cited

U.S. PATENT DOCUMENTS

| 460,940 A | 10/1891 | Baugii |
|---|---|---|
| 3,857,395 A | 12/1974 | Johnson et al. |

(Continued)

FOREIGN PATENT DOCUMENTS

| EP | 0 557 963 A1 | 9/1993 |
|---|---|---|
| EP | 1 336 391 A1 | 8/2003 |

(Continued)

OTHER PUBLICATIONS

Extended European Search Report dated Sep. 5, 2017 in connection with European Application No. 17167634.9.

(Continued)

*Primary Examiner* — Alexander J Orkin (74) *Attorney, Agent, or Firm* — Wolf, Greenfield & Sacks, P.C.

(57) ABSTRACT

A hernia repair device is provided which may include a soft tissue repair prosthesis and an expandable device configured to be removably connected with the soft tissue repair prosthesis. When expanded, the expandable device may be configured to position the soft tissue repair prosthesis adjacent a hernia defect. The soft tissue repair prosthesis may include at least one loop or slit configured to receive a portion of the expandable device. The prosthesis may include a tether to hoist, locate or position the soft tissue repair prosthesis. The expandable device may include indicia for positioning the prosthesis relative to the edge of the hernia defect.

19 Claims, 8 Drawing Sheets

(56) References Cited

U.S. PATENT DOCUMENTS

| | | |
|---|---|---|
| 3,863,639 A | 2/1975 | Kleaveland |
| 3,874,388 A | 4/1975 | King et al. |
| 4,055,861 A * | 11/1977 | Carpentier ............ A61F 2/2448 623/2.36 |
| 4,685,447 A | 8/1987 | Iversen et al. |
| 4,769,038 A | 9/1988 | Bendavid et al. |
| 4,823,815 A | 4/1989 | Watson et al. |
| 5,011,481 A * | 4/1991 | Myers .................... A61B 17/04 606/1 |
| 5,116,357 A | 5/1992 | Eberlach |
| 5,176,692 A | 1/1993 | Wilk |
| 5,263,969 A | 11/1993 | Phillips |
| 5,309,896 A | 5/1994 | Moll et al. |
| 5,333,624 A | 8/1994 | Tovey |
| 5,350,388 A | 9/1994 | Epstein |
| 5,361,752 A | 11/1994 | Moll et al. |
| 5,366,460 A | 11/1994 | Eberbach |
| 5,370,650 A | 12/1994 | Tovey et al. |
| 5,395,383 A | 3/1995 | Adams et al. |
| 5,397,332 A | 3/1995 | Kammerer et al. |
| 5,405,360 A | 4/1995 | Tovey |
| 5,527,264 A | 6/1996 | Moll et al. |
| 5,575,759 A | 11/1996 | Moll et al. |
| 5,607,443 A | 3/1997 | Kierturakis |
| 5,702,416 A | 12/1997 | Kierturakis |
| 5,743,851 A | 4/1998 | Moll et al. |
| 5,769,864 A | 6/1998 | Kugel |
| 5,797,960 A | 8/1998 | Stevens et al. |
| 5,824,082 A | 10/1998 | Brown |
| 5,836,871 A | 11/1998 | Wallace et al. |
| 5,836,961 A | 11/1998 | Kierturakis |
| 5,957,939 A | 9/1999 | Heaven et al. |
| 6,168,608 B1 | 1/2001 | Echeverry et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,224,616 B1 | 5/2001 | Kugel |
| 6,258,113 B1 | 7/2001 | Adams et al. |
| 6,302,897 B1 | 10/2001 | Rousseau |
| 6,312,442 B1 | 11/2001 | Kierturakis |
| 6,379,368 B1 | 4/2002 | Corcoran et al. |
| 6,488,653 B1 | 12/2002 | Lombardo |
| 6,551,241 B1 | 4/2003 | Schultz |
| 6,565,590 B2 | 5/2003 | Kierturakis et al. |
| 6,575,988 B2 * | 6/2003 | Rousseau ......... A61B 17/00234 606/151 |
| 6,638,292 B2 | 10/2003 | Adams |
| 6,663,647 B2 | 12/2003 | Reiley et al. |
| 6,679,900 B2 | 1/2004 | Kierturakis |
| 6,685,714 B2 | 2/2004 | Rousseau |
| 6,702,827 B1 | 3/2004 | Lund et al. |
| 6,755,868 B2 | 6/2004 | Rousseau |
| 6,866,676 B2 | 3/2005 | Kierturakis |
| 6,913,614 B2 | 7/2005 | Marino et al. |
| 7,048,698 B2 | 5/2006 | Whalen et al. |
| 7,101,381 B2 | 9/2006 | Ford et al. |
| 7,128,073 B1 | 10/2006 | van der Burg et al. |
| 7,235,042 B2 | 6/2007 | Vanden Hoek et al. |
| 7,273,489 B2 | 9/2007 | Boudjemline |
| 7,544,213 B2 | 6/2009 | Adams |
| 7,678,123 B2 | 3/2010 | Chanduszko |
| 7,744,617 B2 | 6/2010 | Lunsford et al. |
| 7,780,683 B2 | 8/2010 | Roue et al. |
| 7,947,054 B2 | 5/2011 | Eldar et al. |
| 8,016,851 B2 | 9/2011 | Dillon et al. |
| 8,043,381 B2 | 10/2011 | Hestad et al. |
| 8,372,112 B2 | 2/2013 | Christianson et al. |
| 8,500,762 B2 | 8/2013 | Sholev et al. |
| 8,920,370 B2 | 12/2014 | Sholev et al. |
| 8,920,445 B2 | 12/2014 | Sholev |
| 9,439,643 B2 | 9/2016 | Darois et al. |
| 9,504,548 B2 | 11/2016 | Darois et al. |
| 9,642,689 B2 | 5/2017 | Sholev et al. |
| 9,687,332 B2 | 6/2017 | Sholev et al. |
| 9,808,331 B2 | 11/2017 | Felix et al. |
| 9,861,462 B2 | 1/2018 | Sholev et al. |
| 9,993,324 B2 | 6/2018 | Sholev |
| 10,166,093 B2 | 1/2019 | Felix et al. |
| 2002/0133236 A1 | 9/2002 | Rousseau |
| 2003/0004581 A1 | 1/2003 | Rousseau |
| 2004/0073257 A1 | 4/2004 | Spitz |
| 2004/0087980 A1 | 5/2004 | Ford et al. |
| 2004/0092970 A1 | 5/2004 | Xavier |
| 2004/0097792 A1 | 5/2004 | Moll et al. |
| 2004/0167557 A1 | 8/2004 | Kieturakis et al. |
| 2004/0172048 A1 * | 9/2004 | Browning ............ A61F 2/0063 606/151 |
| 2004/0236363 A1 | 11/2004 | Kieturakis |
| 2005/0033318 A1 | 2/2005 | Miller |
| 2005/0049635 A1 | 3/2005 | Leiboff |
| 2005/0059854 A1 * | 3/2005 | Hoek .................... A61F 2/2481 600/37 |
| 2005/0171569 A1 | 8/2005 | Girard et al. |
| 2006/0247586 A1 | 11/2006 | Voegele et al. |
| 2007/0066980 A1 | 3/2007 | Leahy |
| 2007/0078477 A1 | 4/2007 | Heneveld et al. |
| 2007/0100369 A1 | 5/2007 | Cragg et al. |
| 2007/0185506 A1 | 8/2007 | Jackson |
| 2007/0260179 A1 | 11/2007 | Sholev et al. |
| 2008/0033461 A1 | 2/2008 | Koeckerling et al. |
| 2008/0065229 A1 | 3/2008 | Adams |
| 2008/0167729 A1 * | 7/2008 | Nelson .................. A61F 2/0063 623/23.72 |
| 2008/0195121 A1 | 8/2008 | Eldar et al. |
| 2009/0012350 A1 | 1/2009 | Tihon |
| 2009/0082792 A1 | 3/2009 | Koyfman et al. |
| 2009/0192605 A1 * | 7/2009 | Gloss .................. A61B 5/1076 623/2.11 |
| 2009/0254103 A1 | 10/2009 | Deutsch |
| 2010/0069947 A1 | 3/2010 | Sholev et al. |
| 2010/0137999 A1 | 6/2010 | Shohat |
| 2010/0292718 A1 | 11/2010 | Sholev et al. |
| 2011/0112560 A1 | 5/2011 | Sholev |
| 2011/0295283 A1 | 12/2011 | Darois et al. |
| 2013/0218179 A1 | 8/2013 | Sholev et al. |
| 2013/0231526 A1 | 9/2013 | Felix et al. |
| 2014/0051915 A1 | 2/2014 | Sholev et al. |
| 2015/0196377 A1 | 7/2015 | Sholev et al. |
| 2015/0202035 A1 | 7/2015 | Sholev |
| 2017/0290577 A1 | 10/2017 | Sholev et al. |
| 2018/0092725 A1 | 4/2018 | Felix et al. |
| 2018/0147040 A1 | 5/2018 | Sholev et al. |
| 2018/0368962 A1 | 12/2018 | Sholev |

FOREIGN PATENT DOCUMENTS

| | | |
|---|---|---|
| EP | 1 454 599 A2 | 9/2004 |
| GB | 2 397 239 A | 7/2004 |
| JP | 2000-501634 A | 2/2000 |
| JP | 2007-275203 A | 10/2007 |
| JP | 2008-520372 A | 6/2008 |
| WO | WO 95/30374 A1 | 11/1995 |
| WO | WO 96/00531 A1 | 1/1996 |
| WO | WO 97/021461 A1 | 6/1997 |
| WO | WO 2005/046511 A2 | 5/2005 |
| WO | WO 2006/040760 A2 | 4/2006 |
| WO | WO 2006/055823 A2 | 5/2006 |
| WO | WO 2007/030676 A2 | 3/2007 |
| WO | WO 2007/115110 A2 | 10/2007 |
| WO | WO 2008/045635 A2 | 4/2008 |
| WO | WO 2008/065653 A1 | 6/2008 |
| WO | WO 2009/050717 A2 | 4/2009 |

OTHER PUBLICATIONS

Extended European Search Report dated Oct. 13, 2017 in connection with European Application No. EP 09827885.

International Search Report and Written Opinion dated Jan. 26, 2010 for PCT/US2009/006223.

(56) References Cited

OTHER PUBLICATIONS

International Preliminary Report on Patentability for Application No. PCT/US2009/006223 dated Jun. 3, 2011.

\* cited by examiner

SOFT TISSUE REPAIR PROSTHESIS, EXPANDABLE DEVICE, AND METHOD OF SOFT TISSUE REPAIR

RELATED APPLICATIONS

This application is a continuation of U.S. application Ser. No. 13/130,625, entitled "SOFT TISSUE REPAIR PROSTHESIS, EXPANDABLE DEVICE, AND METHOD OF SOFT TISSUE REPAIR," filed on Jul. 11, 2011, which is a national stage filing under 35 U.S.C. § 371 of international application PCT/US2009/006223, entitled "SOFT TISSUE REPAIR PROSTHESIS, EXPANDABLE DEVICE, AND METHOD OF SOFT TISSUE REPAIR," filed on Nov. 20, 2009, which was published under PCT Article 21(2) in English.

This application also claims the benefit of 35 U.S.C. § 119(e) to U.S. Provisional Application Ser. No. 61/199,884, entitled "HERNIA REPAIR DEVICE AND TECHNIQUE," filed on Nov. 21, 2008, and U.S. Provisional Application Ser. No. 61/247,163, entitled "BALLOON DEPLOYMENT SYSTEM," filed Sep. 30, 2009, all of which are hereby incorporated by reference in their entirety.

FIELD OF INVENTION

The present invention is directed to a soft tissue repair prosthesis, an expandable device, and to a method of soft tissue repair.

BACKGROUND OF INVENTION

One technique for repairing a soft tissue defect, such as an abdominal wall hernia, involves inserting an implantable prosthesis, such as a mesh patch or plug, into an intra-abdominal space, positioning the prosthesis relative to the wall defect, and then, if desired, securing the prosthesis with tacks, sutures, and/or adhesives.

To deliver the prosthesis intra-abdominally, the prosthesis may be rolled up, folded or otherwise collapsed into a reduced profile and then inserted through a small incision or a trocar and into the intra-abdominal space. The prosthesis is then unfurled and positioned relative to the defect.

SUMMARY OF INVENTION

In one illustrative embodiment, a hernia repair device is provided which includes a soft tissue repair prosthesis and at least one loop extending from the prosthesis. The at least one loop has a predetermined size configured to receive a portion of an expandable device to removably connect the prosthesis with the expandable device.

In another illustrative embodiment, a hernia repair device is provided which includes a soft tissue repair prosthesis having at least one slit therethrough, where the at least one slit has a predetermined size configured to receive a portion of an expandable device to removably connect the prosthesis with the expandable device.

In yet another illustrative embodiment, a hernia repair device is provided which includes a soft tissue repair prosthesis having a first side and a second side, and at least one attachment component coupled to the prosthesis and extending outwardly from the first side of the prosthesis. The attachment component is configured to receive a portion of an expandable device to removably connect the prosthesis with the expandable device. The hernia repair device further includes a tether coupled to the prosthesis and extending outwardly from the second side of the prosthesis, where manipulation of the tether allows hoisting, locating and/or positioning of the soft tissue repair prosthesis.

In yet a further illustrative embodiment, a hernia repair device is provided which includes an expandable device configured to be removably connected with a soft tissue repair prosthesis, where the expandable device includes indicia for referencing a predetermined location for positioning an edge of a hernia defect relative to the prosthesis such that the prosthesis overlaps the edge of the defect a predetermined distance.

In another illustrative embodiment, a method of delivering a soft tissue repair prosthesis is provided. The method includes removably connecting at least one loop of a soft tissue repair prosthesis with a portion of an expandable device, and expanding the expandable device.

In another illustrative embodiment, a method of delivering a soft tissue repair prosthesis is provided. The method includes removably connecting at least one slit of a soft tissue repair prosthesis with an expandable device by inserting a portion of the expandable device into the at least one slit, and expanding the expandable device.

In yet another illustrative embodiment, a method of repairing a hernia defect is provided. The method includes removably connecting at least one attachment component coupled to a first side of a soft tissue repair prosthesis with an expandable device to removably connect the soft tissue repair prosthesis with the expandable device, inserting the prosthesis and the expandable device into an abdominal space, expanding the expandable device, and manipulating a tether coupled to a second side of the soft tissue repair prosthesis to hoist, locate or position the soft tissue repair prosthesis.

In a further illustrative embodiment, a method of repairing a hernia defect is provided. The method includes inserting a soft tissue repair prosthesis and an expandable device into an abdominal space where the expandable device is removably connected to the soft tissue repair prosthesis and wherein the expandable device includes indicia referencing a predetermined location, expanding the expandable device, and positioning the prosthesis around a hernia defect in an abdominal wall by positioning an edge of the hernia defect at the indicia referencing the predetermined location such that the prosthesis overlaps the edge of the defect a predetermined distance.

Various embodiments of the present invention provide certain advantages. Not all embodiments of the invention share the same advantages and those that do may not share them under all circumstances.

Further features and advantages of the present invention, as well as the structure of various embodiments that incorporate aspects of the invention are described in detail below with reference to the accompanying drawings.

BRIEF DESCRIPTION OF DRAWINGS

The foregoing and other objects and advantages of the invention will be appreciated more fully from the following drawings, wherein like reference characters designate like features, in which.

DETAILED DESCRIPTION

Aspects of the present invention are directed to a soft tissue repair prosthesis, such as a patch, plug, or patch and plug combination, for repairing, augmenting or reconstructing a muscle or tissue wall, such as a chest wall or abdominal wall, and that has particular application for repairing a hernia defect and for reconstruction of the chest wall. An expandable device may be provided for delivering, locating and/or positioning the soft tissue repair prosthesis at the surgical site. The soft tissue repair prosthesis may be carried by, tethered to, or otherwise operatively connected with the expandable device, such that manipulation of the expandable device will effect the shape, location and/or positioning of the soft tissue repair prosthesis. The expandable device may have a reduced configuration suitable for introduction to the surgical site and an expanded configuration for deploying, locating and/or positioning the soft tissue repair prosthesis. Expansion of the expandable device, when carrying or otherwise integrated with the soft tissue repair prosthesis, may cause the soft tissue repair prosthesis to transform from a reduced delivery profile to an enlarged shape suitable for the desired procedure, such as extending over, under, or filling a hernia defect. The expandable device may be in the form of a balloon or other inflatable bladder, or other construction suitable for delivery in a reduced profile and expansion to a larger size. The soft tissue repair prosthesis may be mounted to, or otherwise integrated with, the expandable device, and then the combined components may be reduced in size, such as by rolling, folding, or otherwise collapsing, and then inserting through a trocar or small incision into the abdominal cavity or other surgical site. Expansion of the expandable device, such as by inflation where the expandable device is in the form of a balloon, will in turn cause the soft tissue repair prosthesis to move into an expanded configuration suitable for the intended procedure. For example, where the soft tissue repair prosthesis is a mesh sheet and has been rolled up with an associated balloon, inflation of the balloon will cause the mesh sheet to unroll or otherwise expand into an enlarged shape which can then be positioned relative to the defect.

Aspects of the present invention are directed to arrangements for operatively connecting an expandable device with a soft tissue repair prosthesis. In one embodiment, the expandable device and soft tissue repair prosthesis are detachably connected. For example, and without limitation, one or more loops or other attachment features may releasably connect the expandable device and soft tissue repair prosthesis. The loops may loosely connect the components together in the reduced profile, or the loops may not contribute to attachment of the expandable device and soft tissue repair prosthesis until one or both of the expandable device and soft tissue repair prosthesis are in an expanded configuration.

Other aspects of the present invention are directed to various approaches to hoist, locate, center or position the prosthesis relative to the defect, and yet further aspects of the present invention are directed to indicia on the expandable device for positioning the prosthesis relative to the hernia defect.

Figure 1:
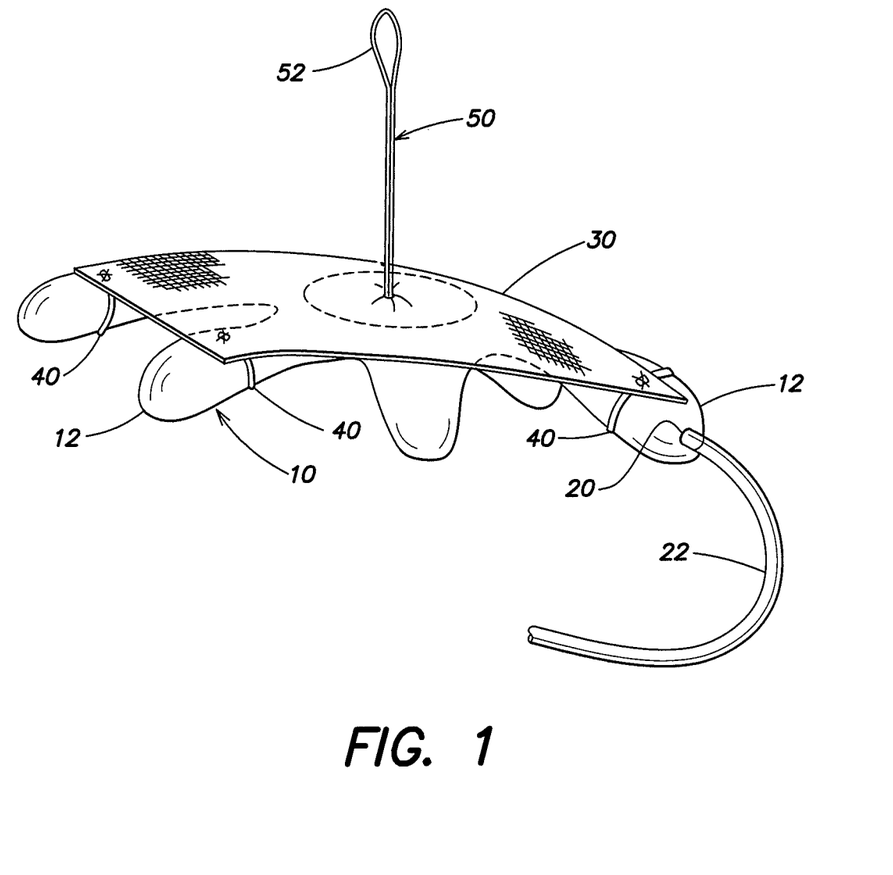
FIG. 1 is a perspective view of an expandable device and soft tissue repair prosthesis according to one embodiment of the present invention.
Figure 2:
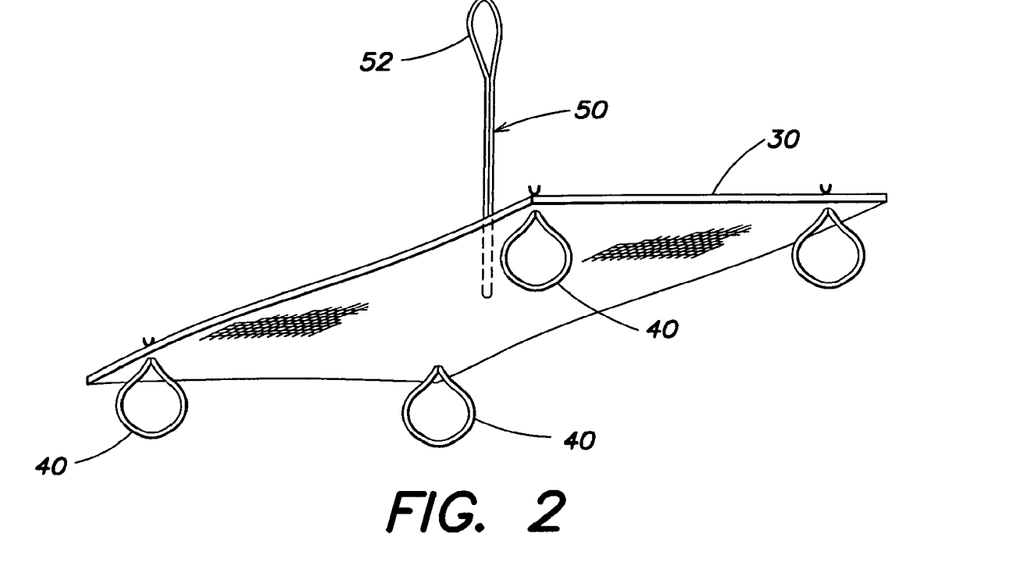
FIG. 2 is a perspective view of the soft tissue repair prosthesis shown in FIG. 1.
Figure 3:
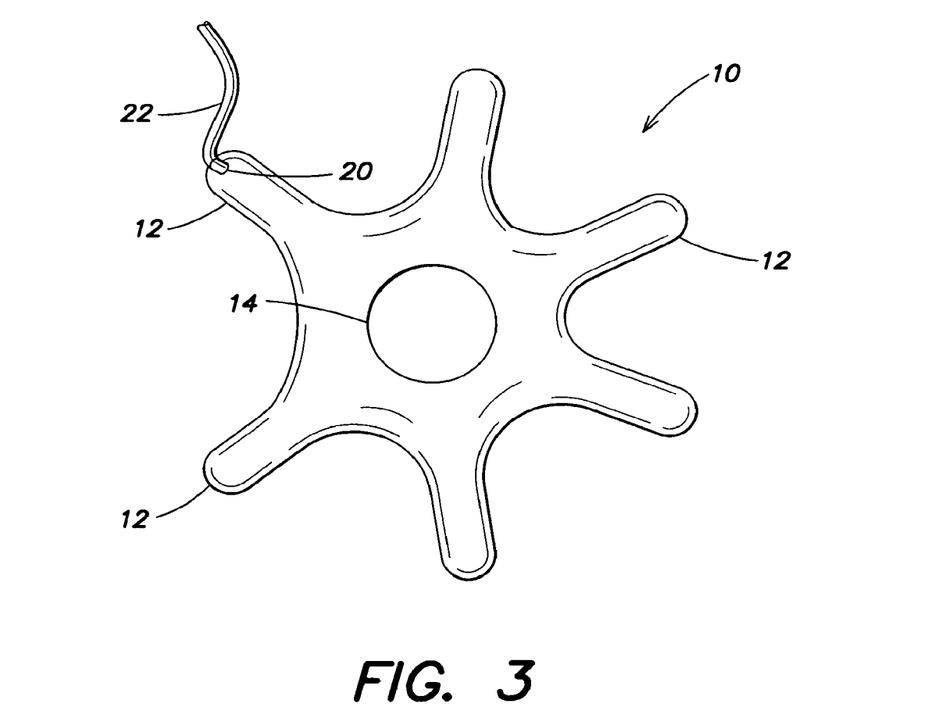
FIG. 3 is a top view of the expandable device shown in FIG. 1.

Turning to FIGS. 1-3, the expandable device has a plurality of outwardly extending arms 12. In this embodiment, the expandable device 10 is shaped like a starfish. As discussed in greater detail below, it should be appreciated that the expandable device may be shaped differently in other embodiments. For example, it is contemplated that the expandable device may be circular, rectangular, lattice shaped or irregular shaped as the invention is not so limited.

As shown in FIG. 3, the expandable device 10 may have an open center portion 14. The open portion may minimize the size or bulk of the expandable device when the expandable device 10 is rolled or folded into a reduced profile configuration. This may assist with the insertion of the expandable device 10, such as through a small incision or a trocar. In one embodiment, the expandable device is asymmetric about the axis which the expandable device is folded or rolled. In this respect, overlap of the arms 12 of the expandable device 10 is minimized if not avoided, reducing the overall profile of the collapsed expandable device. Smaller profiles may be desired to facilitate or permit use with narrow trocar diameters and small incisions.

As shown in FIGS. 1 and 3, an inflation port 20 is positioned on the end of a radially extending arm 12 of the expandable device. As set forth below, in another embodiment, the inflation port 20 may extend from a different location of the expandable device, and may for example extend from a center portion of the expandable device 10. An inflation tube 22 runs to the inflation port 20. The inflation tube 22 may be detachably secured to the inflation port 20 so that the tube 22 can be removed after inflation. The inflation tube 22 may pass through a trocar (not shown) to outside of the patient for connection to an inflation source, such as a syringe. The invention is not limited to a particular inflation medium. A gas, such as air, may be employed, as may be a liquid, such as saline. Other suitable mediums will be apparent to one of skill in the art. Further, the expandable device is not limited to inflatable configurations and other arrangements that have a slender configuration suitable for delivery and an expanded configuration for deployment, locating and/or positioning of the soft tissue repair prosthesis are contemplated.

The expandable device 10 may be removably connected with the soft tissue repair prosthesis 30 by one or more attachment components, including, but not limited to sutures, adhesives, or mechanical fasteners including hook and loop fasteners, rivets, and the like. For example, in one embodiment, an adhesive may be used to detachably connect the prosthesis 30 and the expandable device 10. It is contemplated that a sugar adhesive may be used that dissolves when wetted.

In one embodiment, the attachment component is at least one loop 40 extending from the prosthesis 30. The loop may have a variable size or, instead, have a predetermined size compatible for securing with a portion of the expandable device. For example, the loop may be sized to connectably receive a portion of the expandable device when it reaches an expanded configuration. The loops may define an opening that closely fits around the connecting portion of the expandable device only in the expanded configuration, or the loops may closely fit around the connecting portion in both the reduced profile and expanded configuration. The loops may be compliant or non-compliant, and the loop opening may expand in response to expansion of the expandable device. For example, as illustrated in FIGS. 1 and 2, a plurality of loops 40 may extend from the soft tissue repair prosthesis 30 and one or more arms 12 of the expandable device 10 may extend into the loops 40, removably connecting the expandable device with the soft tissue repair prosthesis. In this respect, the loops may be similar to a belt loop and portions of the expandable device may be configured to fit in the loops. These loops may be formed of a resorbable or a non-resorbable material, as the invention is not limited in this respect. It should be appreciated that the loops 40 may be secured to the prosthesis as shown in FIG. 2 and thereafter secured to the expandable device. It is also contemplated that the loops 40 may initially be wrapped around the expandable device and thereafter secured to the prosthesis as the invention is not so limited. It also is contemplated that the one or more loops might be formed on the expandable device with complementary attachment arrangements being provided on the soft tissue repair prosthesis.

It should be appreciated that the size of the loop 40 is based upon the size of the portion of the expandable device 10 that would be received within the loop 40. In one embodiment, the loop has a diameter of approximately 2 cm to approximately 10 cm. In another embodiment, the loop has a diameter of at least approximately 5 cm. One of skill in the art would recognize that the loop 40 may be sized to be slightly larger than the expandable device to accommodate the expandable device 10 within the loop 40.

In the particular embodiment illustrated in FIGS. 1 and 2, the loops 40 are spaced apart and discretely formed. As illustrated, each loop may terminate in a knot or weld that prevents the loop 40 from detaching from the prosthesis 30. As discussed in greater detail below, in another embodiment, the loops 40 are part of an integral structure, such as a running suture.

It should be appreciated that the loops 40 may be formed from a variety of materials, as the invention is not limited in this respect. In one embodiment the loops 40 are formed from suture material, such as but not limited to polyglycolic acid (PGA), or Vicryl® which is a polyglactin absorbable suture material. In another embodiment, the loops 40 are formed from soft tissue repair fabric, such as, but not limited to expanded polytetrafluorethylene (ePTFE). The loops may be configured to encourage tissue infiltration, to resist tissue infiltration, or to provide localized and differing tissue infiltration properties. For example, and without limitation, the loops may be formed of a barrier material, include a barrier material, and/or include a coating or surface treatment that discourages, or encourages, tissue ingrowth.

It should also be recognized that the expandable device 10 may also be formed from a variety of materials, as the invention is not limited in this respect. In one embodiment, the expandable device is formed of polyurethane, and may, for example, be formed of nylon coated polyurethane. In an embodiment where the expandable device 10 is inflatable, the expandable device may be formed of two layers of nylon coated polyurethane that together form a chamber for the introduction of air.

As illustrated in FIGS. 1 and 2, a tether 50 may be coupled to the soft tissue repair prosthesis 30 to assist in hoisting, locating and/or positioning the soft tissue repair prosthesis, and the expandable device if it still is connected therewith. As shown, in one embodiment, the soft tissue repair prosthesis has a first side and a second side where at least one attachment component (such as the loops 40) extend from the first side of the prosthesis and the tether 50 extends from the second side of the prosthesis. The tether 50 may be formed from a suture, soft tissue repair fabric, or other material as should be apparent to one of skill in the art. The tether may be resorbable or permanent. The tether may be singular or include a plurality of tether segments, for example the tether 50 may include a plurality of sutures or strips that are spaced about the prosthesis. The tether 50 may be secured approximately at the center of the prosthesis 30, or surrounding the center of the prosthesis, such that the center of the prosthesis can more readily be aligned with the center of the hernia defect. However, as should be apparent to one of skill in the art, the invention is not limited to a tether that focuses forces at or about the center of the soft tissue repair prosthesis. With the soft tissue repair prosthesis deployed and expanded in the intra-abdominal space, a suture-grasping device (not shown) may be provided to grasp the tether and hoist the prosthesis 30 towards the defect and/or to position the soft tissue repair prosthesis against the abdominal wall. As shown, in one embodiment, the tether 50 includes a loop 52 adapted for grasping and manipulation by a surgical instrument or the physician's hands. Once the soft tissue repair prosthesis 30 is positioned relative to the defect, sutures, fasteners, adhesives or the like may be applied to fixate the prosthesis 30 in place.

After placement of the prosthesis 30, the loops 40 may be left in place or, instead, removed. As an example, and without limitation, an instrument may be employed to cut the loops. It may be desirable to separate the soft tissue repair prosthesis from the expandable device prior to removing the loops. The soft tissue repair prosthesis may be separable from an expanded expandable device and, in certain embodiments, it may facilitate separation by at least partially reducing the size of the expandable device (e.g., such as by at least partially deflating where the expandable device is a balloon). As mentioned above, it is also contemplated that the loops 40 are resorbable.

It is also contemplated that in one embodiment, one or more of the loops 40 may be used as transfacial sutures to secure the prosthesis 30 around the defect. In other words, the expandable device 10 may be detached from the prosthesis 30 without cutting and/or removing some or all of the loops 40. Such loops 40 themselves, or cut into strands, may then be used to secure the prosthesis. It also is contemplated that sutures, distinct from the tether, may be pre-attached to the soft tissue repair prosthesis and used to secure the implant relative to the defect.

A method of repairing a hernia defect in accordance with the present invention includes one or more of the steps of: detachably securing an expandable device to a prosthesis, rolling or folding the prosthesis and detachably secured expandable device into a slender configuration, inserting the prosthesis and expandable device into the intra-intra-abdominal space, inflating the expandable device to unfurl the mesh, pulling on a tether coupled to the prosthesis to hoist the prosthesis up against the abdominal wall, fixating the prosthesis against the abdominal wall, detaching the expandable device from the prosthesis, and removing the expandable device from the intra-intra-abdominal space.

One method of delivering a soft tissue repair prosthesis includes removably connecting at least one loop of a soft tissue repair prosthesis with a portion of an expandable device, and expanding the expandable device. The method may also include inserting the prosthesis and the expandable device into an abdominal space, positioning the prosthesis around a hernia defect in an abdominal wall, securing the prosthesis to the abdominal wall, and detaching the prosthesis and the expandable device.

Another method of repairing a hernia defect includes removably connecting at least one attachment component coupled to a first side of a soft tissue repair prosthesis with an expandable device to removably connect the soft tissue repair prosthesis with the expandable device, inserting the prosthesis and the expandable device into an abdominal space, expanding the expandable device, and manipulating a tether coupled to a second side of the soft tissue repair prosthesis to hoist, locate or position the soft tissue repair prosthesis. The method may further include securing the prosthesis to the abdominal wall, and detaching the prosthesis and the at least one attachment component.

The prosthesis 30 may be formed of a porous material, such as a knit, woven or non-woven fabric, or may be composed of a solid, substantially non-porous, or microporous material. The prosthesis may be formed of one or more layers of the same or dissimilar material. The prosthesis may be formed with portions that are tissue infiltratable and other portions that are non-tissue infiltratable, providing selected areas of the repair device with different tissue ingrowth and adhesion resistant properties. The prosthesis may be formed of permanent material, resorbable material, or a combination of permanent and resorbable materials. It should be appreciated that the prosthesis may be formed of any biologically compatible material, synthetic or natural, suitable for repairing a tissue or muscle wall defect as would be apparent to one of skill in the art. The prosthesis may be formed into a patch, plug or combination patch and plug.

In one embodiment, the prosthesis 30 is formed from a mesh fabric, such as a sheet of knitted polypropylene monofilament mesh fabric. The sheet may have a thickness of approximately 0.014 inches and may be knitted from polypropylene monofilament having a diameter of approximately 0.0042 inches. When implanted, the polypropylene mesh promotes rapid tissue or muscle ingrowth into and around the mesh structure. Alternatively, other surgical materials which are suitable for tissue or muscle reinforcement and defect correction may be utilized including BARD MESH (available from C.R. Bard, Inc.), SOFT TISSUE PATCH (microporous ePTFE—available from W.L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Biologic materials, including XENMATRIX, COLLAMEND, and ALLOMAX (all available from C.R. Bard, Inc.) or COOK SURGISIS (available from Cook Biomedical, Inc.) may also be used. Resorbable materials, including polyglactin (VICRYL—available from Ethicon, Inc.) and polyglycolic acid (DEXON—available from US Surgical, Inc.), may be suitable for applications involving temporary correction of tissue or muscle defects. It also is contemplated that the fabric may be formed from multifilament yarns and that any suitable method, such as knitting, weaving, braiding, molding and the like, may be employed to form the mesh material. It should be appreciated that when the soft tissue repair prosthesis is in the form of a sheet, it may be configured in many shapes, including, but not limited to flat, concave, and convex, and may, for example, be in the form of a square, rectangle, circle, or ellipse.

Figure 4:
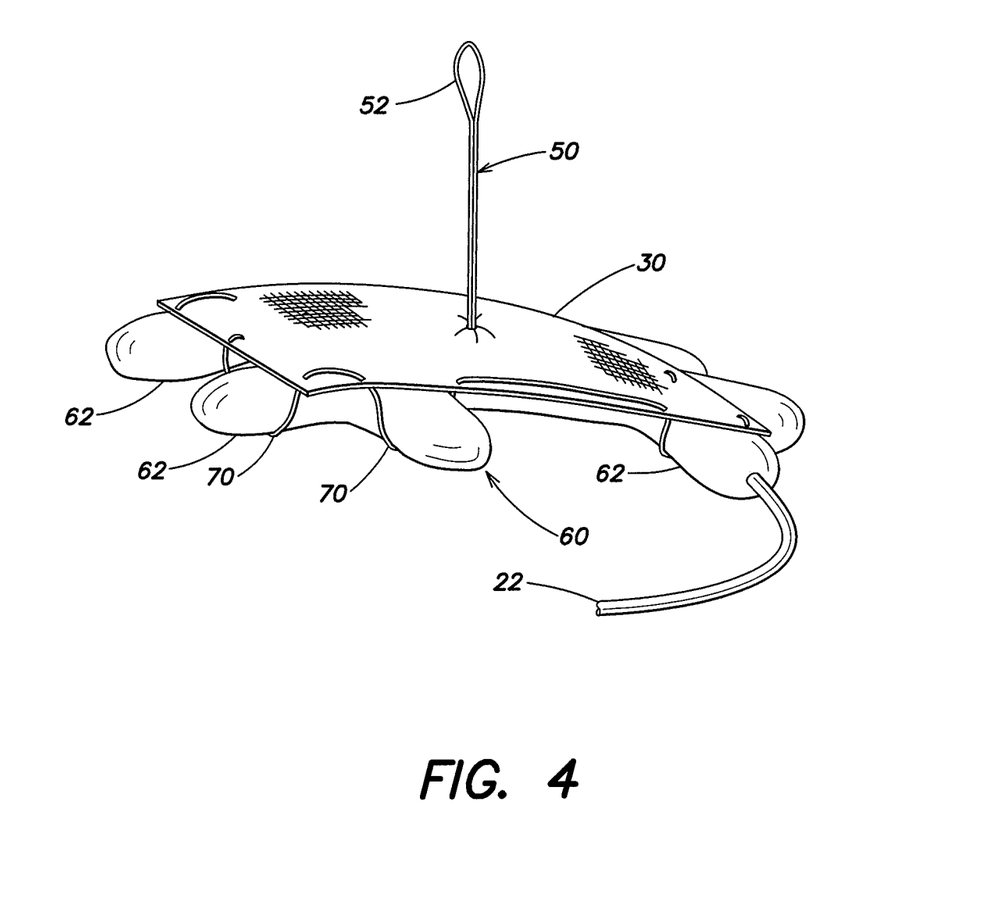
FIG. 4 is a perspective view of an expandable device and soft tissue repair prosthesis according to another embodiment of the present invention.
Figure 5:
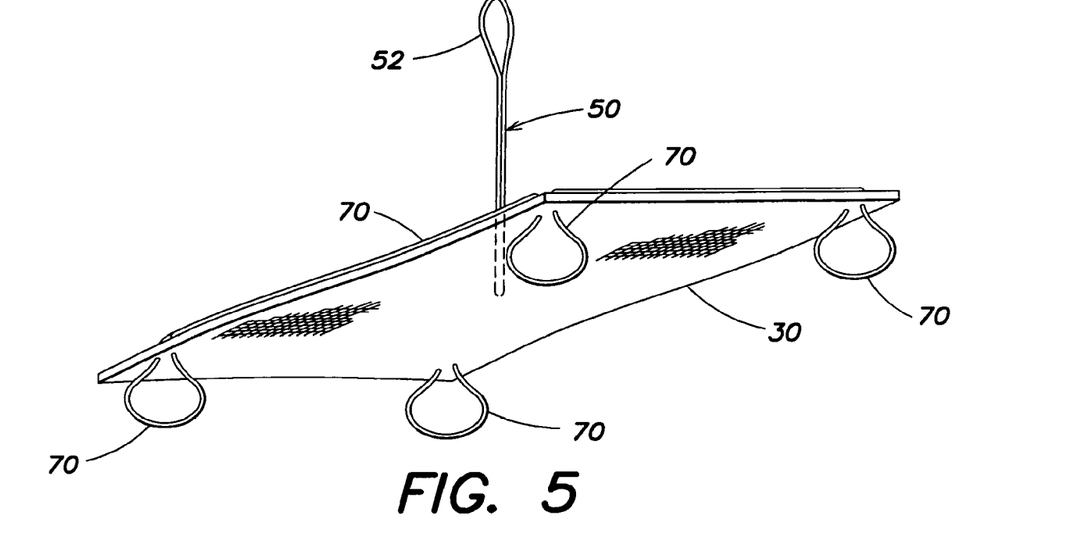
FIG. 5 is a perspective view of the soft tissue repair prosthesis shown in FIG. 4.
Figure 6:
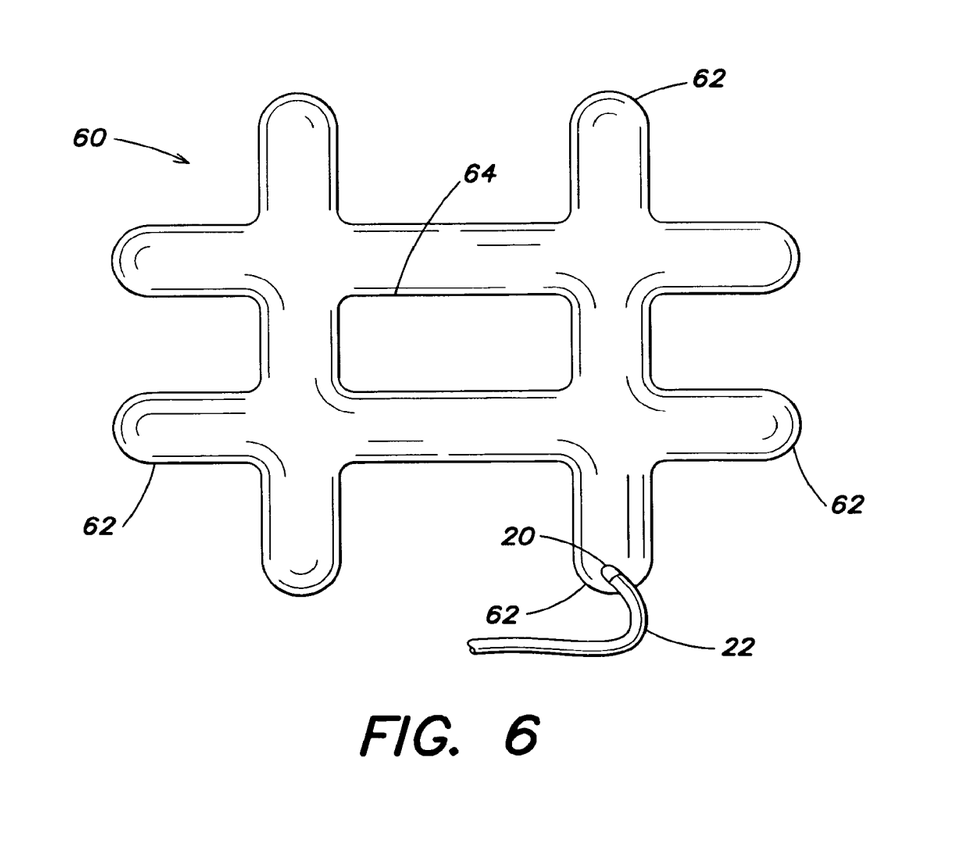
FIG. 6 is a top view of the expandable device shown in FIG. 4.

Turning now to FIGS. 4-6, another illustrative embodiment of an expandable device 60 is discussed in greater detail. In this embodiment, the expandable device 60 is lattice shaped and has a plurality of outwardly extending arms 62. The expandable device 60 includes an open center portion 64 which, as mentioned above, may minimize the size or bulk of the expandable device 60 when the expandable device is rolled or folded into a reduced profile configuration. As shown in FIGS. 4 and 6, an inflation port 20 allows the expandable device to be inflated or otherwise expanded into a larger profile configuration. In this particular embodiment, the inflation port 20 is positioned on an end of an outwardly extending arm 62 of the expandable device. It should be recognized that the expandable device 62 may be inflated with a gas, such as air, or the expandable device may be filled with a liquid, such as saline, to reach an expanded profile. Other inflation mediums are contemplated as should be apparent to one of skill in the art.

As shown in FIGS. 4 and 5, a plurality of loops 70 are secured to the prosthesis 30 and the loops 70 are configured to receive portions of the expandable device 60, removably connecting the expandable device and the prosthesis. The plurality of loops 70 may be part of a continuum, or integrated structure, such as a running suture, such that a plurality of loops 70 are formed with the same length of suture. Similar to the embodiment shown in FIG. 1, the loops 70 extend through the prosthesis and one or more arms 62 of the expandable device 60 extend into the loops 70 to secure the expandable device with the prosthesis. It should be appreciated that in one embodiment, the size of the loops 70 may be adjustable. For example, in one embodiment, the size of the loops 70 may be adjustable by pulling the loop 70 through the prosthesis. As set forth above, the prosthesis 30 may also include a tether 50, which further may be provided with a loop 52 on one end, to assist in hoisting, locating and/or positioning the soft tissue repair prosthesis.

Once the prosthesis 30 is secured in place, the loops 70 may be cut and removed from the expandable device/prosthesis interface. It is also contemplated that the loops 70 may not need to be cut to detach the expandable device from the prosthesis, as the loops 40 may be configured such that the arm 62 of the expandable device may slide out of the loop and/or the loops may be configured to be absorbable within the body. The expandable device 60 is deflated or otherwise transformed into its reduced profile configuration and the expandable device may be withdrawn from the intra-abdominal space through a trocar.

As mentioned above, an inflation tube 22 may be detachably secured to the inflation port 20 and the inflation tube 22 may pass through a trocar (not shown) to enable inflation of the expandable device from outside of the body. It is also contemplated that a one-way inflation valve could be used so that once the expandable device is inflated, the inflation tube 22 may be removed from the trocar to free up the trocar for other instruments. The inflation tube 22 may either be detached from the inflation port 20 and removed from the body, or the inflation tube may be tucked back into the intra-abdominal space and may be removed with the expandable device.

Furthermore, it is also contemplated that the expandable device may be inflated through an inflation port positioned on the underside of the expandable device. The inflation port may be grasped to both inflate and manipulate the expandable device.

Figure 7:
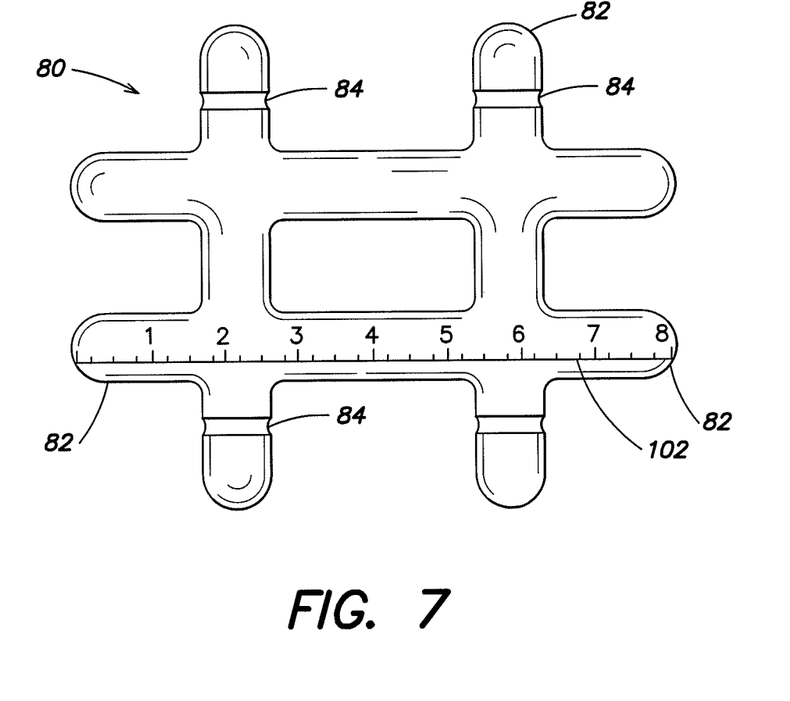
FIG. 7 is a top view of an expandable device according to another embodiment.
Figure 8:
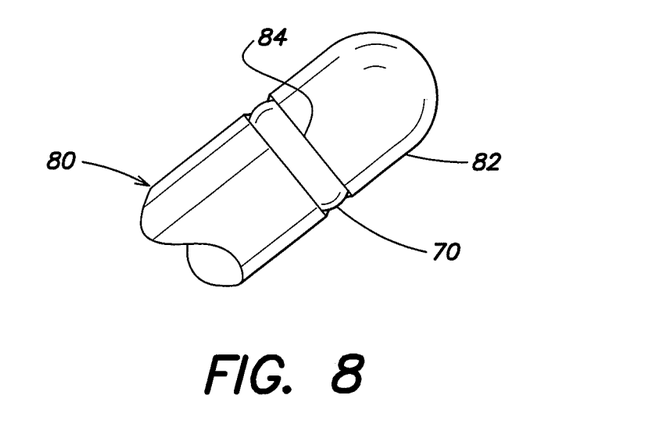
FIG. 8 is a detailed view of a portion of an expandable device according to one embodiment.

FIGS. 7 and 8 illustrate a feature for facilitating connection of one or more loops with the expandable device. At least one indentation 84 is provided on the expandable device which receives a loop 40, 70. In the embodiment shown in FIG. 8, the indentations 84 are reduced dimensioned regions of the expandable device and the indentations may be shaped to prevent the loop 40, 70 from undesirably sliding off and detaching from the expandable device 80. In one embodiment, the indentations 84 are circumferential, such that they extend substantially around the arm of the expandable device, although an interrupted or partially circumferential indentation also is contemplated. In another embodiment, the indentation may be formed by the region between two spaced apart protrusions on the expandable device.

Once the prosthesis is secured in place over the defect, the loop 40, 70 may be cut away from the indentation 84, or the loop 40, 70 may be slid over the indentation 84 to detach the expandable device 80 from the prosthesis 30. It should be appreciated that once the expandable device is deflated or otherwise transformed into its reduced profile configuration, it may be easier to dislodge the loop from the indentation 84 in the expandable device 80.

Figure 9:
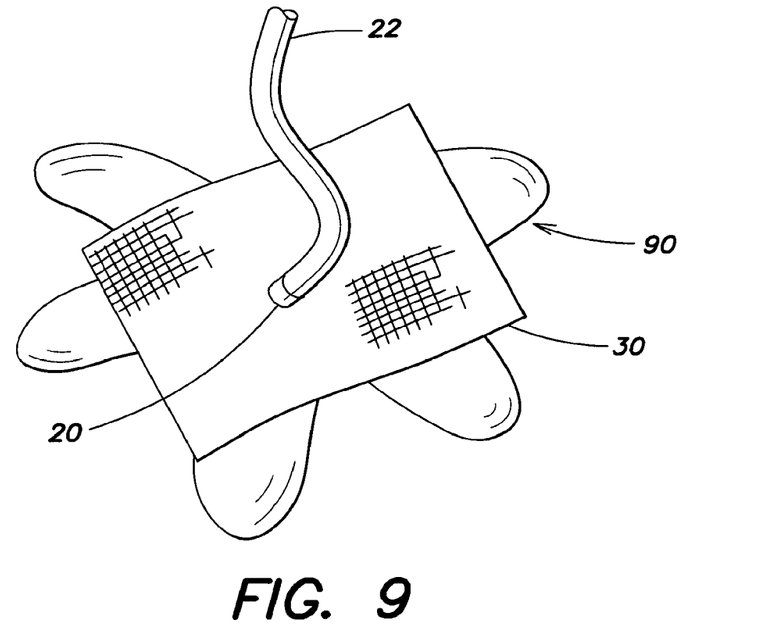
FIG. 9 is a top view of an expandable device according to another embodiment.

As mentioned above, a tether 50 may be secured to the prosthesis to assist in hoisting the prosthesis and the expandable device up to the defect. In another embodiment, the inflation tube 22 may be used to hoist the prosthesis and the expandable device up to the defect. In particular, as shown in FIG. 9, in one embodiment, the inflation tube 22 may be secured to an inflation port 20 at approximately the center of the prosthesis 30 and the inflation tube 22 may pass through the prosthesis 30. After the prosthesis 30 is inserted into the intra-abdominal space and positioned below the hernia defect, a suture-grasping device (not shown) may be passed through the skin in the middle of the defect. The inflation tube 22 may be pulled upward with the grasping device to hoist the prosthesis 30 into position against the abdominal wall. As shown, in one embodiment, the inflation tube 22 is secured to the center of the prosthesis 30 such that the prosthesis 30 can more readily be aligned with the center of the hernia defect. Once the prosthesis 30 is pulled up and positioned relative to the defect, the prosthesis 30 may be fixated to the margins of the defect using sutures, fasteners, adhesives or the like in accordance with any of the techniques known to one of ordinary skill in the art. As shown in the embodiment of FIG. 9, the inflation tube 22 may extend through the prosthesis, and may for example, extend through the mesh of the prosthesis. After inflation, the inflation tube 22 may be disconnected from the inflation port 20 such that the tube 22 can be removed through the defect. Thereafter, the expandable device 90 can be detached from the prosthesis and deflated, such that the expandable device can be removed from the body.

Figure 10:
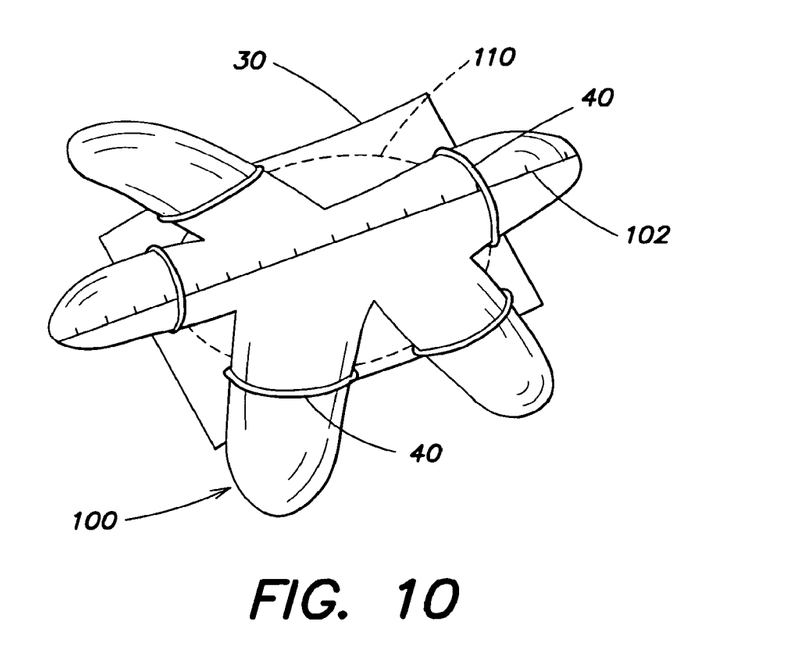
FIG. 10 is a bottom view of an expandable device and soft tissue repair prosthesis according to one embodiment of the present invention.

FIG. 10 illustrates a bottom view of an expandable device 100 and a prosthesis 30 positioned to cover a defect 110 (shown in dashed lines as it may not be visible through the prosthesis 30). In this embodiment, the expandable device 100 has indicia 102, which, in this particular embodiment is similar to a ruler and may assist in centering the prosthesis 30 relative to the defect 110 and/or measuring the amount that the prosthesis overlaps the defect. In one embodiment, the indicia 102 may include numeric indicia. Although the defect 110 may not be visible through the prosthesis, the location of the defect may be detected during a palpation, as the prosthesis 30 may move slightly into the defect 110, indicating the perimeter of the defect. By adjusting the orientation of the expandable device, the indicia 102 may be used to measure the amount of overlap of the prosthesis in one or more directions. The position of the prosthesis 30 may then be adjusted accordingly. For example, the indicia 102 may be used for referencing a predetermined location for positioning an edge of a hernia defect relative to the prosthesis such that the prosthesis overlaps the edge of the defect a predetermined distance.

FIG. 7 illustrates another embodiment of an expandable device 80 having indicia 102. The expandable device 100 may further include indicia such as, but not limited to markers, arrows, or other indicia to help to orient the expandable device and prosthesis and/or to indicate selected extraction points on the expandable device where the expandable device should be grasped to remove the expandable device from the body. The indicia may also be used to show the long axis about which the expandable device may be rolled to insert into the body. Furthermore, indicia may be used to indicate the locations of the attachment components. In one embodiment, the indicia is visible, and may for example include colored markings. In another embodiment, the indicia may only be visible with special imaging tools, and in yet another embodiment, the indicia may be tactile such that the indicia includes a surface that a user can sense by touch.

Figure 13:
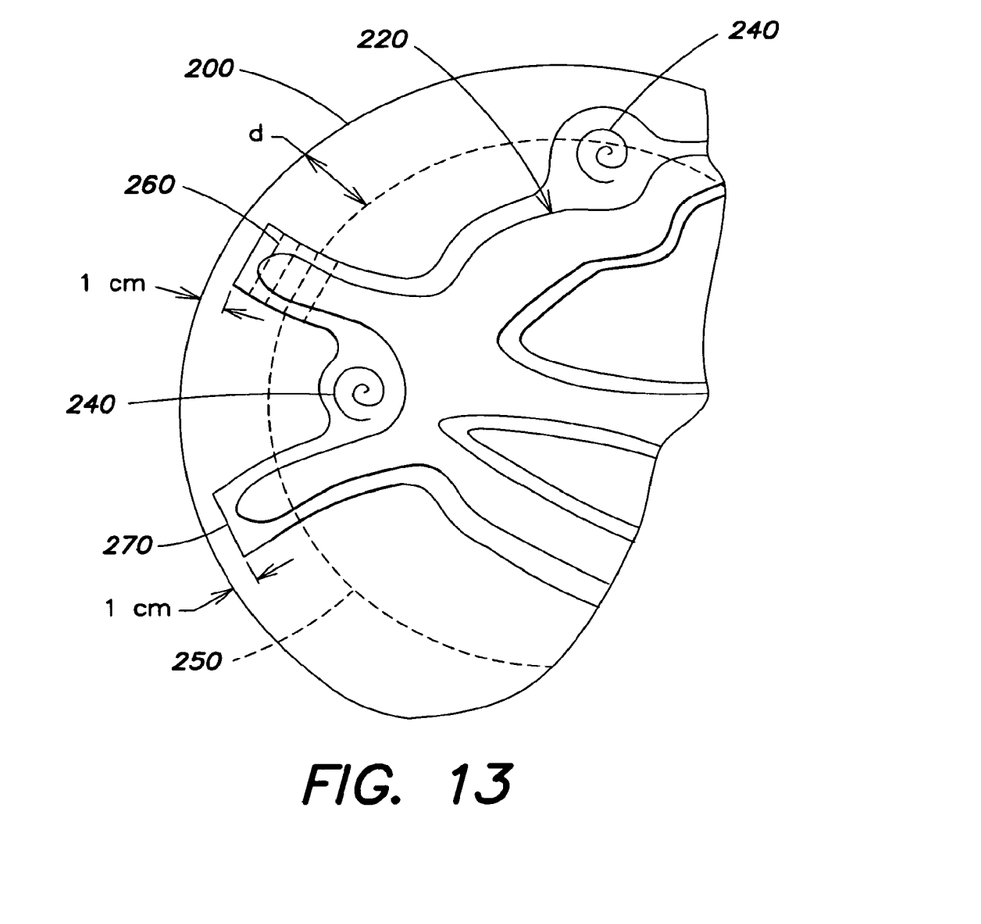
FIG. 13 is a partial view of an expandable device and soft tissue repair prosthesis according to another embodiment.

Turning now to FIG. 13, another embodiment of an expandable device with indicia is illustrated. For simplification, only a portion of an expandable device 220 and prosthesis 200 are illustrated, and as discussed above, a plurality of attachment components 240 removably connect the expandable device 220 with the prosthesis 200. In this embodiment, the expandable device 220 includes a tab 270 which includes indicia 260. This indicia is for referencing a predetermined location for positioning an edge 250 of a hernia defect (shown in dashed lines) relative to the prosthesis 200 such that the prosthesis 200 overlaps the edge 250 of the defect a predetermined distance "d". In this particular embodiment, the prosthesis 200 is secured with the expandable device 220 such that the outer perimeter of the prosthesis is approximately 1 cm away from the edge of the tab 270. The tab 270 includes indicia 260 which includes a plurality of markings that are spaced apart approximately 1 cm. Thus, a user is able to use the indicia 260 such that the prosthesis 200 overlaps the edge 250 of the defect a predetermined distance "d" which is equal to 4 cm in the illustrative embodiment. In one embodiment, the predetermined distance is between approximately 3 cm-approximately 5 cm. However, it should be appreciated that the predetermined distance may vary based upon the particular defect and prosthesis.

One method of repairing a hernia defect includes inserting a soft tissue repair prosthesis and an expandable device into an abdominal space where the expandable device is removably connected to the soft tissue repair prosthesis and where the expandable device includes indicia referencing a predetermined location, expanding the expandable device, and positioning the prosthesis around a hernia defect in an abdominal wall by positioning an edge of the hernia defect at the indicia referencing the predetermined location such that the prosthesis overlaps the edge of the defect a predetermined distance.

Figure 11:
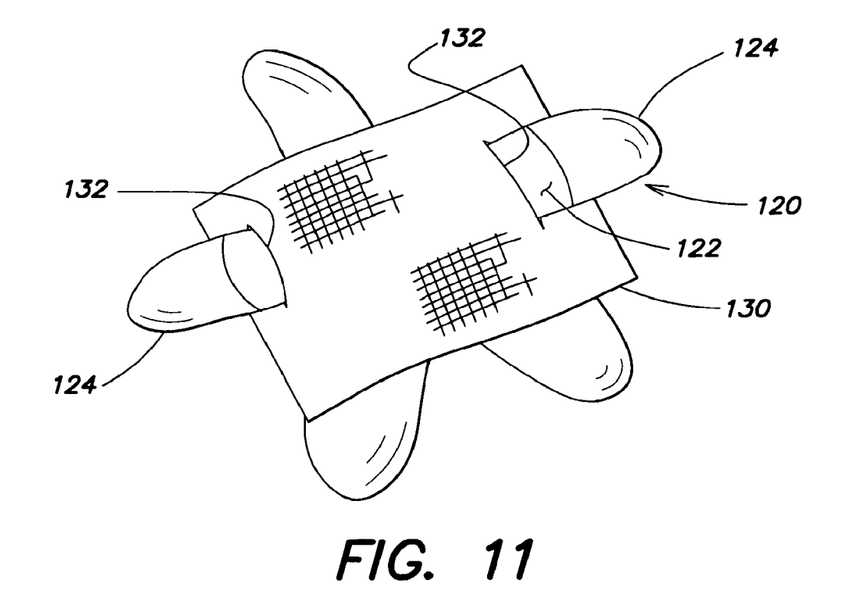
FIG. 11 is a perspective view of an expandable device and prosthesis according to yet another embodiment of the present invention.

As illustrated in FIG. 11, in one embodiment, the prosthesis 130 may include at least one slit 132 having a predetermined size configured to receive a portion of the expandable device 120 to removably connect the prosthesis to the expandable device. In this particular embodiment, the expandable device 120 has a plurality of arms 122 that are configured to slide into a plurality of slits 132 in the prosthesis. The expandable device 120 may be removably connected with the prosthesis 130 when in its reduced or deflated profile configuration, and then, as discussed above, the expandable device may be expanded or inflated once the prosthesis 130 and expandable device are positioned in the body near the defect. Once the prosthesis 130 is positioned over the defect, the expandable device may be detached from the prosthesis by pulling or sliding the arms 122 of the expandable device 120 out from the slits 132 in the prosthesis 130. As set forth above, detaching the expandable device 120 from the prosthesis 130 may be more easily facilitated after the expandable device 120 is deflated or otherwise transformed back into its reduced profile configuration.

Figure 12:
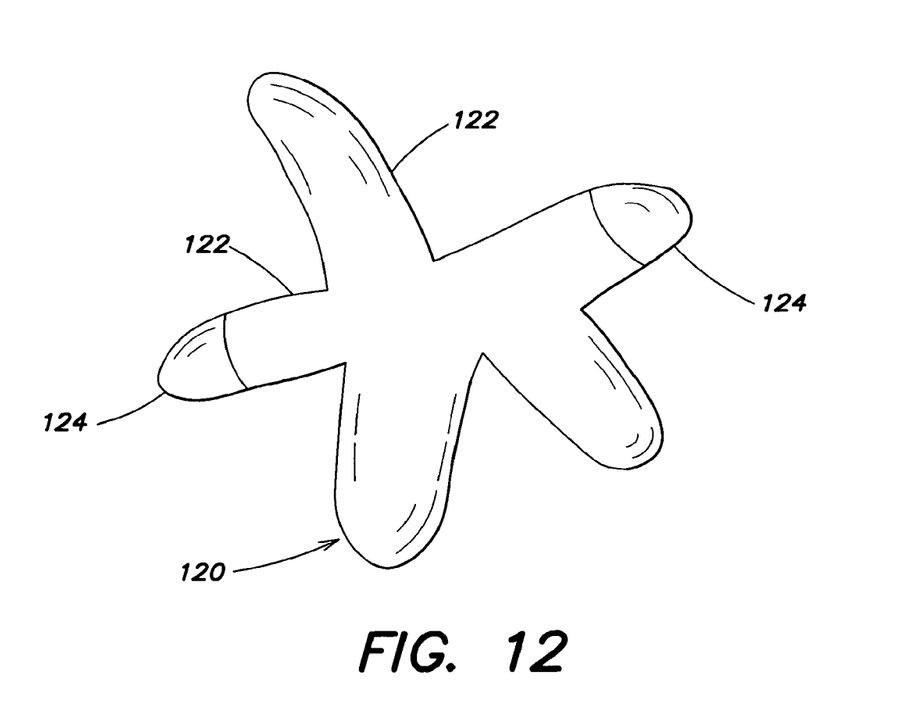
FIG. 12 is a top view of an expandable device according to one embodiment.

In one embodiment, end portions of the expandable device 120 may remain in a reduced profile when other portions of the expandable device are expanded or inflated. For example, as shown in the embodiment illustrated in FIG. 12, the end portions of arms 122 may include non-expandable portions 124. These non-expandable portions 124 may be passed through the slits 132 in the prosthesis 130 and they may assist in retaining the arms of the expandable device within the slit 132 after the expandable device is expanded or inflated. Also, these non-expandable portions 124 may help to keep the prosthesis 130 lying substantially flush with the defect and the abdominal wall.

It should be appreciated that the size of the slit 132 is based upon the size of the portion of the expandable device 120 that would be received within the slit 132. In one embodiment, the slit has a diameter of approximately 2 cm to approximately 10 cm. In another embodiment, the slit has a diameter of at least approximately 5 cm. One of skill in the art would recognize that the slit 132 may be sized to be slightly larger than the expandable device to accommodate the expandable device 10 within the slit 132.

One method of delivering a soft tissue repair prosthesis includes removably connecting at least one slit of a soft tissue repair prosthesis with an expandable device by inserting a portion of the expandable device into the at least one slit, and expanding the expandable device.

The present invention also contemplates other systems for expanding and/or unfurling the prosthesis. Although inflatable expandable devices (either filled with a gas or a liquid) are primarily discussed above, other expandable devices that don't rely on inflation are contemplated. For example, and without limitation, also contemplated are an expandable device that includes telescoping portions and/or umbrella-like spokes, an expandable device including shape memory material, and an expandable device that resiliently expands into an enlarged configuration.

It should be appreciated that various embodiments of the present invention may be formed with one or more of the above-described features. The above aspects and features of the invention may be employed in any suitable combination as the present invention is not limited in this respect. It should also be appreciated that the drawings illustrate various components and features which may be incorporated into various embodiments of the present invention. For simplification, some of the drawings may illustrate more than one optional feature or component. However, the present invention is not limited to the specific embodiments disclosed in the drawings. It should be recognized that the present invention encompasses embodiments which may include only a portion of the components illustrated in any one drawing figure, and/or may also encompass embodiments combining components illustrated in multiple different drawing figures.

It should be understood that the foregoing description of various embodiments of the invention are intended merely to be illustrative thereof and that other embodiments, modifications, and equivalents of the invention are within the scope of the invention recited in the claims appended hereto.

The invention claimed is:

1. A hernia repair device, comprising:
    an expandable device;
    an implantable soft tissue repair prosthesis comprising a mesh fabric configured to be attached to soft tissue by a fixation device and having a plurality of slits therethrough, wherein each of the plurality of slits has a predetermined size configured to receive a portion of the expandable device to removably connect the prosthesis with the expandable device and to position the prosthesis adjacent a hernia defect; and
    a tether coupled to the prosthesis at a location separate and distinct from a plurality of slits, wherein manipulation of the tether allows hoisting, locating or positioning of the soft tissue repair prosthesis,
    wherein the expandable device is configured to expand from a reduced profile to an expanded configuration to expand the prosthesis, and
    wherein the expandable device is removably engaged in each of the plurality of slits.

2. The hernia repair device of claim 1, wherein the expandable device includes at least one arm and at least one slit of the plurality of slits is configured to receive at least a portion of the arm to removably connect the prosthesis with the expandable device.

3. The hernia repair device of claim 2, wherein an end portion of the at least one arm is non-expandable, and wherein the non-expandable end portion is configured to be passed through the at least one slit.

4. The hernia repair device of claim 1
    wherein the expandable device includes numeric indicia at an edge of the expandable device for referencing a predetermined location for positioning an edge of a hernia defect relative to the prosthesis such that the prosthesis overlaps the edge of the defect a predetermined distance.

5. The hernia repair device of claim 4, wherein the indicia includes a ruler with a plurality of markings to position the prosthesis relative to the defect.

6. The hernia repair device of claim 4, wherein the indicia is visible.

7. The hernia repair device of claim 4, wherein the indicia is visible with imaging.

8. The hernia repair device of claim 4, wherein the indicia is tactile.

9. The hernia repair device of claim 4, wherein the soft tissue repair prosthesis is formed from a mesh fabric.

10. The hernia repair device of claim 1, wherein the expandable device being configured to expand the prosthesis comprises the expandable device being configured to unroll the prosthesis.

11. The hernia repair device of claim 1, wherein the fixation device includes one or more selected from the group consisting of sutures, fasteners, adhesives, and tacks.

12. A hernia repair device, comprising:
    an expandable device;
    an implantable soft tissue repair prosthesis comprising a mesh fabric and having at least one slit therethrough, wherein the mesh fabric has a first portion and a second portion, wherein the second portion has different tissue ingrowth properties than the first portion, and wherein the at least one slit has a predetermined size configured to receive a portion of the expandable device to removably connect the prosthesis with the expandable device; and a tether coupled to the prosthesis at a location separate and distinct from the at least one slit, wherein manipulation of the tether allows hoisting, locating or positioning of the soft tissue repair prosthesis, wherein the expandable device is configured to expand from a reduced profile to an expanded configuration to expand the prosthesis, and wherein the expandable device is removably engaged in the at least one slit.

13. The hernia repair device of claim 12, wherein the at least one slit includes a plurality of slits, wherein the plurality of slits each have a predetermined size configured to receive a portion of the expandable device to removably connect the prosthesis with the expandable device to position the prosthesis adjacent a hernia defect.

14. The hernia repair device of claim 13, wherein the expandable device includes at least one arm and the at least one slit is configured to receive at least a portion of the arm to removably connect the prosthesis with the expandable device.

15. The hernia repair device of claim 14, wherein an end portion of the at least one arm is non-expandable, and wherein the non-expandable end portion is configured to be passed through the at least one slit.

16. A method of delivering a soft tissue repair prosthesis, comprising:

providing a soft tissue repair prosthesis comprising a mesh fabric configured to be attached to soft tissue by a fixation device and having a plurality of slits therethrough;

removably connecting the soft tissue repair prosthesis with a portion of an expandable device by inserting the portion of the expandable device through at least one slit of the plurality of slits of the soft tissue repair prosthesis;

expanding the expandable device from a reduced profile to an expanded configuration to expand the prosthesis; and manipulating a tether coupled to the prosthesis at a location separate and distinct from the plurality of slits, wherein manipulation of the tether allows hoisting, locating or positioning of the soft tissue repair prosthesis, wherein the expandable device is removable from the at least one slit such that the prosthesis is removable from the expandable device without cutting or removing the at least one slit.

17. The method of claim 16, further comprising inserting the prosthesis and the expandable device into an abdominal space.

18. The method of claim 17, further comprising:

positioning the prosthesis around a hernia defect in an abdominal wall;

securing the prosthesis to the abdominal wall; and detaching the prosthesis and the expandable device.

19. The method of claim 16, further comprising using numeric indicia at an edge of the expandable device for referencing a predetermined location for positioning an edge of a hernia defect relative to the prosthesis such that the prosthesis overlaps the edge of the defect a predetermined distance.

* * * * *

UNITED STATES PATENT AND TRADEMARK OFFICE
CERTIFICATE OF CORRECTION

PATENT NO. : 10,548,703 B2
APPLICATION NO. : 15/299578
DATED : February 4, 2020
INVENTOR(S) : Roger E. Darois et al.

Page 1 of 1

It is certified that error appears in the above-identified patent and that said Letters Patent is hereby corrected as shown below:

In the Claims

At Column 12, Claim 1, Line 21, replace "distinct from a plurality of slits" with --distinct from the plurality of slits--

At Column 12, Claim 4, Line 38, replace "The hernia repair device of claim 1" with --The hernia repair device of claim 1,--

Signed and Sealed this
Twenty-fourth Day of March, 2020

Andrei Iancu
*Director of the United States Patent and Trademark Office*